United States Patent
Zhang et al.

(10) Patent No.: US 10,519,183 B2
(45) Date of Patent: Dec. 31, 2019

(54) AMINE SOLVATE OF SODIUM-GLUCOSE LINKED TRANSPORTER INHIBITOR, AND PREPARATION METHOD AND APPLICATION THEREOF

(71) Applicant: Youngene Therapeutics Co., Ltd., Shanghai (CN)

(72) Inventors: Lei Zhang, Shanghai (CN); Yuan Wang, Shanghai (CN)

(73) Assignee: Youngene Therapeutics Co., Ltd., Shanghai (CN)

( * ) Notice: Subject to any disclaimer, the term of this patent is extended or adjusted under 35 U.S.C. 154(b) by 0 days.

(21) Appl. No.: 16/096,119

(22) PCT Filed: Mar. 27, 2017

(86) PCT No.: PCT/CN2017/078309
§ 371 (c)(1),
(2) Date: Oct. 24, 2018

(87) PCT Pub. No.: WO2017/190568
PCT Pub. Date: Nov. 9, 2017

(65) Prior Publication Data
US 2019/0135848 A1   May 9, 2019

(30) Foreign Application Priority Data

May 4, 2016  (CN) .......................... 2016 1 0296693

(51) Int. Cl.
*C07H 15/00* (2006.01)
*C07H 15/04* (2006.01)
*C07H 9/04* (2006.01)
*C07H 7/04* (2006.01)
*C07H 19/01* (2006.01)
*A61K 31/7048* (2006.01)
*C07H 1/00* (2006.01)

(52) U.S. Cl.
CPC ......... *C07H 19/01* (2013.01); *A61K 31/7048* (2013.01); *C07H 1/00* (2013.01); *C07H 7/04* (2013.01); *C07H 9/04* (2013.01); *C07H 15/00* (2013.01); *C07H 15/04* (2013.01); *C07B 2200/13* (2013.01)

(58) Field of Classification Search
None
See application file for complete search history.

(56) References Cited

FOREIGN PATENT DOCUMENTS

| CN | 101056853 A | 10/2007 | |
| CN | 104513283 A | 4/2015 | |
| WO | WO-2015027963 A1 | 3/2015 | |
| WO | WO-2015032272 A1 * | 3/2015 | ............. A61K 31/00 |
| WO | WO-2015032272 A1 | 3/2015 | |
| WO | WO-2017190568 A1 | 11/2017 | |

OTHER PUBLICATIONS

"International Application No. PCT/CN2017/078309, International Search Report and Written Opinion dated Jun. 28, 2017", (Jun. 28, 2017), 14 pgs.
Brittain, Harry G., "Polymorphism in Pharmaceutical Solids", Copyright 1999 Marcel Dekker Inc., ISBN: 0-8247-0237-9, Discovery Laboratories, Inc., Milford, New Jersey, (1999), 461 pgs.
Byrn, Stephen R., et al., "Solid-State Chemistry of Drugs, Second Edition", SSCI, West Lafayette, Indiana, 1999 (only abstract available), (1999), 10 pgs.
Mullin, J. W., et al., "Programmed cooling of batch crystallizers", Chemical Engineering Science, 1971, 26, 369-377, (1971), 369-377.
Smith, D. K., "A FORTRAN Program for Calculating X-Ray Powder Diffraction Patterns", Lawrence Radiation Laboratory, Livermore, California, UCRL-7196, Apr. 1963 (only abstract available), (Apr. 1963), 2 pgs.
Yin, Shawn, et al., "Simulated PXRD Patterns in Studies of the Phase Composition and Thermal Behavior of Bulk Crystalline Solids", American Pharmaceutical Review, 2003, 6, 2, 80 (only abstract available), (2003), 1 pg.
"Australian Application No. 2017259388, Examination report No. 1 for standard patent application dated Jan. 22, 2019", (Jan. 22, 2019), 3 pgs.
"Australian Application No. 2017259388, Request to Amend a Complete Specification dated Mar. 25, 2019", (Mar. 25, 2019), 19 pgs.

* cited by examiner

*Primary Examiner* — Traviss C McIntosh, III
(74) *Attorney, Agent, or Firm* — Schwegman Lundberg & Woessner, P.A.

(57) ABSTRACT

Disclosed are an amine solvate of a sodium-glucose linked transporter (SGLT) inhibitor, and a preparation method and application thereof. The SGLT inhibitor is (1S,2S,3S,4R,5S)-5-(3-((2,3-dihydrobenzo[b][1,4]dioxin-6-yl)methyl)-4-ethylbenzyl)-1-(hydroxymethyl)-6,8-dioxabicyclo[3.2.1]octane-2,3,4-triol. Further provided is a crystalline compound of the amine solvate, a pharmaceutical composition comprising the amine solvate, and an application of the amine solvate in preparing an SGLT-inhibiting pharmaceutical product.

19 Claims, 8 Drawing Sheets

AMINE SOLVATE OF SODIUM-GLUCOSE LINKED TRANSPORTER INHIBITOR, AND PREPARATION METHOD AND APPLICATION THEREOF

PRIORITY CLAIM TO RELATED APPLICATIONS

This application is a U.S. national stage filing under 35 U.S.C. § 371 from International Application No. PCT/CN2017/078309, filed on 27 Mar. 2017, and published as WO2017/190568 on 9 Nov. 2017, which claims the benefit under 35 U.S.C. 119 to Chinese Application No. 201610296693.2, filed on 4 May 2016, the benefit of priority of each of which is claimed herein, and which applications and publication are hereby incorporated herein by reference in their entirety.

FIELD OF THE INVENTION

The present invention belongs to the field of drug development, and specifically relates to an amine solvate of sodium-dependent glucose co-transporter inhibitor, and a preparation method and use thereof.

BACKGROUND OF THE INVENTION

Diabetes is a metabolic disorder with recurrent or persistent hyperglycemia. Abnormal levels of blood glucose can lead to serious and chronic complications, including cardiovascular disease, chronic renal failure, retinal damage, nerve damage, microvascular damage and obesity.

In the early stage of diabetes treatment, control of diet and exercise therapy are the preferred method for controlling blood glucose. When control of blood glucose is difficult to achieve with these methods, insulin or oral hypoglycemic drugs are needed for the treatment. There have been a variety of hypoglycemic drugs used currently in clinical treatment, including biguanide compounds, sulfonylurea compounds, insulin resistance improving agents, α-glucosidase inhibitors and the likes. However, these drugs are unable to meet the needs of long-term treatment due to various toxic effects. For example, biguanide compounds can cause lactic acidosis; sulfonylurea compounds can lead to hypoglycemia; insulin resistance improving agents can induce edema and heart failure; and α-glucosidase inhibitors can cause symptoms such as abdominal pain, distention, diarrhea and the likes. In consideration of the above situation, it is necessary to develop a safer and more effective novel anti-diabetic drugs to meet the needs of diabetes treatment.

It has been found that the regulation of glucose transport in cells is mainly achieved by the two protein family members of glucose transporters (GLUTS) (passive transport) and sodium-dependent glucose co-transporters (SGLTs) (active transport). The SGLTs family members with glucose transport function are mainly located in the intestine and the proximal tubule of the kidney and the like. Accordingly, it can be inferred that the SGLTs family members play a key role in glucose absorption in the intestine and glucose reuptake in the kidney; and they have become one of the ideal potential targets for treating diabetes.

In particular, family member SGLT-1 protein is mainly located in the intestinal mucosal cells of the small intestine, with less expression in cardiac muscle and the kidney. It mainly cooperates with GLUTs protein to regulate glucose absorption in the intestine. Another family member SGLT-2 protein is mainly responsible for regulating glucose reuptake in the kidneys due to its high level of expression in the kidneys, when glucose in urine passes through the glomerulus, it can actively attach to the epithelial cells of the renal tubule and be transported into the cells by SGLT-2 and recycled. During this process, SGLT-2 is responsible for 90% of the reabsorption, and the remaining 10% of the reabsorption is done by SGLT-1. The theory of SGLT-2 as a major transporter protein has been further confirmed in animal tests. SGLT-2 mRNA level in rat renal cortex cells is reduced by specific SGLT-2 antisense oligonucleotides, thereby significantly inhibiting the reuptake of glucose in rat kidney. Based on these findings, it can be inferred that if a SGLTs (SGLT-1/SGLT-2) inhibitor is developed, through the regulation of its glucose transport function, it is possible to control intestinal absorption of glucose on the one hand, and on the other hand, to inhibit the reuptake of renal glucose and enhance discharge of glucose from the urine, thereby achieving a more systematic hypoglycemic effect, and becoming an ideal drug for treating diabetes.

Additionally, it has been also found that the SGLTs inhibitor can be useful in the treatment of diabetes-related complications, such as retinopathy, neuropathy, nephropathy, insulin resistance caused by glucose metabolism disorders, hyperinsulinemia, hyperlipidemia, obesity and the like. SGLTs inhibitor can also be combined with the existing therapeutic agents, such as sulfonamides, thiazolidinediones, metformin, insulin and the like, which can reduce the dosage of drugs without affecting the efficacy, so as to avoid or reduce the occurrence of adverse effects and improve the compliance of patients to the treatment.

In summary, as a novel drug for treating diabetes, the SGLTs inhibitor has a good development prospects. Therefore, there is an urgent need to develop an effective compound that is safe and has good pharmacokinetic properties for the treatment of diabetes and related metabolic disorders. The patent application WO2015/032272A1 filed by Jiangsu Hansoh Pharmaceuticals Co., Ltd. in 2015 discloses a series of compounds that inhibit sodium-dependent glucose co-transporter (SGLT), wherein the most representative compound of formula (I) is as follows:

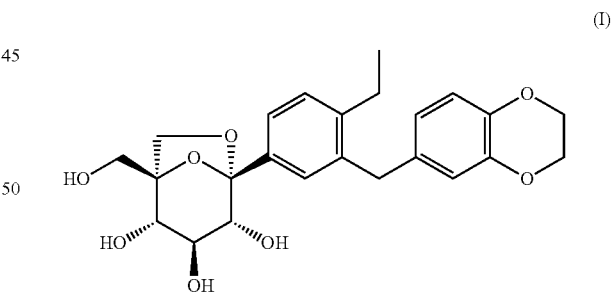

(I)

The chemical name thereof is: (1S,2S,3S,4R,5S)-5-(3-((2,3-dihydrobenzo[b][1,4]dioxin-6-yl)methyl)-4-ethylphenyl)-1-(hydroxymethyl)-6,8-dioxabicyclo[3.2.1]octane-2,3,4-triol. This compound has a very significant inhibitory effect on SGLT2, and also has a significant inhibitory effect on SGLT1, therefore it is expected to be developed as a single inhibitor of SGLT2 or a dual inhibitor of SGLT2/SGLT1. However, this series of compounds are generally in the form of oil or foamy solid due to their structure property, and the skilled person failed to obtain an appropriate aggregation state during the process of drug development. Example 9 of the patent application WO2015/032272A1 merely discloses the compound of formula (I) in an amorphous form, the X-ray powder diffraction pattern thereof is shown in FIG. 8. The impurities contained therein are also difficult to remove by purification. Therefore, there is an urgent need to develop an aggregation form suitable for drug development, so as to meet the requirement of pharmaceutical formulation for clinical research and marketing.

SUMMARY OF THE INVENTION

In order to overcome the defect of the prior art, after in-depth research, the inventor has found that the compound of formula (I) (1S,2S,3S,4R,5S)-5-(3-((2,3-dihydrobenzo[b][1,4]dioxin-6-yl)methyl)-4-ethylphenyl)-1-(hydroxymethyl)-6,8-dioxabicyclo[3.2.1]octane-2,3,4-triol can be combined to an amine reagent, thereby obtaining an amine solvate of the compound of formula (I) in a solid form, especially an amine solvate of the compound of formula (I) in a crystalline form. The resulting amine solvate of the compound of formula (I) can meet the requirement of further drug development. It has a very important clinical application value and is expected to be developed into a new generation of SGLT inhibitor.

In an aspect, the present invention provides an amine solvate of the compound of formula (I) (1S,2S,3S,4R,5S)-5-(3-((2,3-dihydrobenzo[b][1,4]dioxin-6-yl)methyl)-4-ethylphenyl)-1-(hydroxymethyl)-6,8-dioxabicyclo[3.2.1]octane-2,3,4-triol, the amine is selected front the group consisting of methylamine, dimethylamine, ethylamine, diethylamine, propylamine, dipropylamine, tripropylamine 1,2-dimethylpropylamine, cyclopropylamine, diisopropylamine, triethylamine, n-butylamine, isobutylamine, tert-butylamine, sec-butylamine, diisobutylamine, hexylamine, dicyclohexylamine, decylamine, dodecylamine, triethanolamine, allylamine, ethanolamine, 3-propanolamine, isopropanolamine, diisopropanolamine, triisopropanolamine, dimethylethanolamine, diethylethanolamine, ethylenediamine, 1,3-propanediamine, 1,4-butanediamine, 1,5-pentanediamine, 1,6-hexanediamine, morpholine and piperazine.

In a further preferred embodiment, the amine is selected from the group consisting of diethylamine, diisopropylamine, triethanolamine, triisopropanolamine, ethylenediamine and 1,3-propanediamine.

In a further preferred embodiment, the amine solvate of the compound of formula (I) is a solid compound.

In a more further preferred embodiment, the amine solvate of the compound of formula (I) is a crystalline compound.

In a further preferred embodiment, the amine solvate of the compound of formula (I) is a diethylamine solvate of the compound of formula (I).

The X-ray powder diffraction pattern of the diethylamine solvate of the compound of formula (I) comprises peaks at diffraction angle (2θ) of 13.78±0.2°, 17.02±0.2°, 16.48±0.2°, and 12.46±0.2°.

In a further preferred embodiment, the X-ray powder diffraction pattern of the diethylamine solvate of the compound of formula (I) further comprises peaks at diffraction angle (2θ) of 23.94±0.2°, 18.74±0.2°, 18.76±0.2°, 15.72±0.2°, and 20.68±0.2°.

In a more further preferred embodiment, the X-ray powder diffraction pattern of the diethylamine solvate of the compound of formula (I) further comprises peaks at diffraction angle (2θ) of 10.82±0.2°, 21.58±0.2°, 23.26±0.2°, 25.16±0.2°, 25.58±0.2°, and 74.76±0.2°.

In a most preferred embodiment, the X-ray powder diffraction pattern of the diethylamine solvate of the compound of formula (I) comprises substantially the same peaks at diffraction angles (2θ) as shown in Table 1.

TABLE 1

| 2θ (°) | Intensity % |
| --- | --- |
| 8.80 | 10.6 |
| 10.82 | 31.1 |
| 11.56 | 7.7 |
| 12.46 | 42.9 |
| 13.20 | 8.8 |
| 13.78 | 100 |
| 15.72 | 33.4 |
| 16.48 | 43.8 |
| 17.02 | 49.6 |
| 18.74 | 34 |
| 20.10 | 15.5 |
| 20.68 | 32.7 |
| 21.58 | 27.3 |
| 22.12 | 9.2 |
| 23.26 | 24.9 |
| 23.94 | 37.9 |
| 24.26 | 17.8 |
| 25.16 | 23.9 |
| 25.58 | 19.2 |
| 26.48 | 16.6 |
| 27.78 | 8.2 |
| 28.82 | 16.6 |
| 29.42 | 2.6 |
| 30.48 | 4.9 |
| 31.28 | 6.7 |
| 32.74 | 3.2 |
| 35.30 | 5.2 |
| 36.02 | 3.9 |
| 36.88 | 3.3 |
| 39.12 | 6.5 |
| 39.80 | 4.5 |
| 40.80 | 4.2 |
| 41.52 | 4.3 |
| 42.24 | 6.1 |
| 43.28 | 3 |
| 44.24 | 3.9 |

In a more further preferred embodiment, the unit cell of the diethylamine solvate of the compound of formula (I) is orthogonal system, space group, P212121, a=8.2642 (4) Å, b=8.3582 (4) Å, c=39.994 (2) Å, and the unit cell volume is 2762.5 (2) Å$^3$.

In another aspect, the present invention provides a process for preparing the amine solvate of the compound of formula (I), comprising the following steps of:

step 1): contacting the compound of formula (I) with a suitable amine reagent;

step 2): adding an appropriate amount of anti-solvent until the solution appears turbid, or adding a seed crystal, or a combination thereof, then continuing to precipitate a crystal; and step 3): separating solid-liquid to obtain the amine solvate of the compound of formula (I).

In a further preferred embodiment, the amine reagent in step 1) of the process for preparing amine solvate of the compound of formula (I) is a pure liquid amine reagent, an aqueous amine reagent or a mixture of an amine reagent and an organic solvent, and the amine reagent is selected from the group consisting of methylamine, dimethylamine, ethylamine, diethylamine, propylamine, dipropylamine, tripropylamine, 1,2-dimethylpropylamine, cyclopropylamine, diisopropylamine, triethylamine, n-butylamine, isobutylamine, tert-butylamine, sec-butylamine, diisobutylamine, hexylamine, dicyclohexylamine, decylamine, dodecylamine, triethanolamine, ethanolamine, 3-propanolamine, isopropanolamine, diisopropanolamine, triisopropanolamine, dimethylethanolamine, diethylethanolamine, ethylenediamine, 1,3-propanediamine, 1,4-butanediamine, 1,5-pentanediamine, 1,6-hexanediamine, morpholine and piperazine.

In a further preferred embodiment, the contact of the compound of formula (I) with a suitable amine reagent in step 1) can be done by dissolving the compound of formula (I) in a suitable amine reagent, or dissolving the compound of formula (I) in a suitable organic solvent, followed by the addition of a suitable amine reagent.

The dissolution refers to a conventional operation known by those skilled in the art. Heating properly or increasing the amount of solvent can generally be carried out to dissolve the material or to make the solution clear. Modifications or equivalent substitutions of the technical solutions are intended to be included within the scope of the present invention.

In a further preferred embodiment, the anti-solvent in step 2) comprises, but is not limited to, water, n-heptane, n-hexane, isooctane, pentane, cyclohexane, cyclopentane, diethyl ether or a mixture thereof.

In a more further preferred embodiment, the organic solvent used in the process for preparing the amine solvate of the compound of formula (I) comprises, but is not limited to, methanol, ethanol, n-propanol, isopropanol, n-butanol, acetonitrile, acetone, methyl ethyl ketone, tetrahydrofuran, dioxane, N,N-dimethylformamide, dimethyl sulfoxide, ethyl acetate, isopropyl acetate, dichloromethane, trichloroethane, carbon tetrachloride, methyl tert-butyl ether, diisopropyl ether, benzene, toluene, xylene or a mixture thereof.

In another aspect, the present invention provides a pharmaceutical composition comprising a therapeutically effective amount of the amine solvate of the compound of formula (I), and pharmaceutically acceptable carrier.

In another aspect, the present invention relates to the use of the above mentioned amine solvate of the compound of formula (I) or a pharmaceutical composition comprising the same in the preparation of a medicament for inhibiting sodium-dependent glucose co-transporters (SGLTs).

In another aspect, the present invention relates to the use of the above mentioned amine solvate of the compound of formula (I) or a pharmaceutical composition comprising the same in the preparation of a medicament for inhibiting SGLT-1 protein, a medicament for inhibiting SGLT-2 protein, or a medicament for dual inhibiting SGLT-1 protein and SGLT-2 protein.

In another aspect, the present invention relates to the use of an amine solvate of the compound of formula (I) or a pharmaceutical composition comprising the same in the preparation of a medicament for treating or delaying the development or the attack of a disease selected from the group consisting of diabetes, diabetic retinopathy, diabetic neuropathy, diabetic nephropathy, insulin resistance, hyperglycemia, hyperinsulinemia, elevated levels of fatty acids or glycerol, hyperlipidemia, obesity, hypertriglyceridemia, X syndrome, diabetes complications, atherosclerosis and hypertension.

The present invention also relates to the abovementioned amine solvate of the compound of formula (I) or a pharmaceutical composition comprising the same for use as a SGLTs inhibitor, especially a SGLT-1 inhibitor, a SGLT-2 inhibitor, a SGLT-1 and SGLT-2 dual inhibitor.

The present invention also relates to the abovementioned amine solvate of the compound of formula (I) or a pharmaceutical composition comprising the same for use in treating or delaying the development or the attack of diabetes, diabetic retinopathy, diabetic neuropathy, diabetic nephropathy, insulin resistance, hyperglycemia, hyperinsulinemia, elevated levels of fatty acids or glycerol, hyperlipidemia, obesity, hypertriglyceridemia, X syndrome, diabetes complications, atherosclerosis or hypertension.

In another aspect, the present invention provides a method for inhibiting SGLTs, comprising administrating a therapeutically effective amount of the amine solvate of the compound of formula (I) or a pharmaceutical composition comprising the same to a patient in need thereof.

In another aspect, the present invention provides a method for treating diabetes, diabetic retinopathy, diabetic neuropathy, diabetic nephropathy, insulin resistance, hyperglycemia, hyperinsulinemia, elevated levels of fatty acids or glycerol, hyperlipidemia, obesity, hypertriglyceridemia, X syndrome, diabetes complications, atherosclerosis or hypertension, comprising administrating a therapeutically effective amount of the abovementioned amine solvate of the compound of formula (I) or a pharmaceutical composition comprising the same to a patient in need thereof.

DETAILED DESCRIPTION OF THE INVENTION

1. Terms

Figure 1:
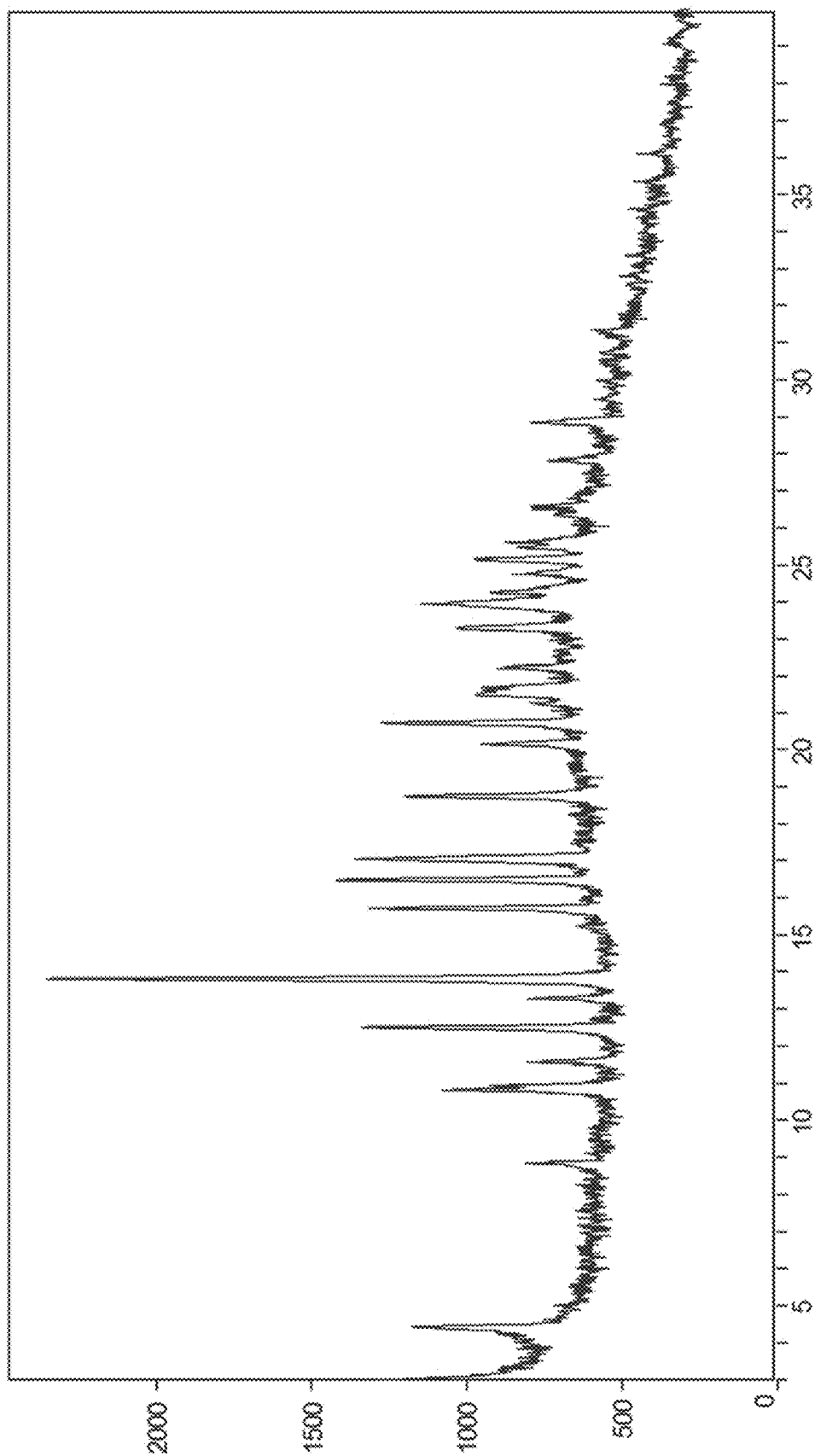
FIG. 1 shows the X-ray powder diffraction pattern of crystal form I; X-axis represents the diffraction peak angle 2θ (°), Y-axis represents the intensity of the peak.

The term "pharmaceutically acceptable", as used herein, refers to those compounds, materials, compositions, and/or dosage forms which are, within the scope of sound medical judgment, suitable for contact with the tissues of human beings and animals without excessive toxicity, irritation, allergic response, or other problem complications commensurate reasonable benefit/risk ratio. In certain preferred embodiments, the crystalline structures of the compound of the present invention is in substantially pure form.

The term "substantially pure", as used herein, means a compound having a purity greater than about 90%, including, for example, about 91%, about 92%, about 93%, about 94%, about 95%, about 96%, about 97%, about 98%, about 99%, and about 100%.

As used herein "polymorph" refers to crystal forms having the same chemical composition but different spatial arrangements of the molecules, atoms, and/or ions forming the crystal. Although polymorphs have the same chemical composition, they differ in packing and geometric arrangement, and can exhibit different physical properties such as melting point, shape, color, density, hardness, deformability, stability, solubility, dissolution rate, and similar properties. Depending on their temperature-stability relationship, two polymorphs can be either monotropic or enantiotropic. For a monotropic system, the relative stability between the two solid phases remains unchanged as the temperature is changed. In contrast, in an enantiotropic system, there exists a transition temperature at which the stability of the two phases is reversed ((Theory and Origin of Polymorphism in "Polymorphism in Pharmaceutical Solids" (1999) ISBN:)-8247-0237). The phenomenon of a compound existing in different crystal structures is called drug polymorphism phenomenon.

Samples of the crystalline structures of the present invention can be provided with substantially pure phase homogeneity, indicating the presence of a dominant amount of a single crystalline structure and optionally minor amounts of one or more other crystalline structures. The presence of more than one crystalline structure of the present invention in a sample can be determined by techniques such as X-ray powder diffraction (XRPD) or solid state nuclear magnetic resonance spectroscopy (SSNMR). For example, in the comparison of an experimentally measured XRPD spectrum (observed) with a simulated XRPD spectrum (calculated), the presence of extra peaks can indicate more than one crystalline structure in the sample. The simulated XRPD can be calculated from single crystal X-ray data (see Smith, D. K., "A FORTRAN Program for Calculating X-Ray Powder Diffraction Patterns," Lawrence Radiation Laboratory, Livermore, Calif., UCRL-7196, April 1963; also see Yin. S., Scaringe, R. P., DiMarco, J., Galella, M. and Gougoutas, J. Z., American Pharmaceutical Review, 2003, 6, 2, 80). Preferably, the crystalline structure has substantially pure phase homogeneity as indicated by less than 10%, preferably less than 5%, and more preferably less than 2% of the total peak area in the experimentally measured XRPD spectrum arising from the extra peaks that are absent in the simulated XRPD spectrum. Most preferred is a crystalline structure of the present invention having substantially pure phase homogeneity with less than 1% of the total peak area in the experimentally measured XRPD spectrum arising from the extra peaks that are absent in the simulated XRPD spectrum.

The various crystalline structures of the present invention can be distinguished from one another through the use of various analytical techniques known to those skilled in the art. Such techniques include, but are not limited to, X-ray powder diffraction (XRPD), differential scanning calorimetry (DSC), and/or thermogravimetric analysis (TGA).

The crystalline structures of the present invention can be prepared by various methods, including for example, crystallization or recrystallization from a suitable solvent, sublimation, growth from a melt, solid state transformation from another phase, crystallization from a supercritical fluid, and jet spray. Techniques for crystallization or recrystallization of crystalline structures from a solvent mixture include, for example, evaporating the solvent, decreasing the temperature of the solvent mixture, crystal seeding in a supersaturated solvent mixture of the molecule and/or salt, lyophilizing the solvent mixture, and adding an anti-solvent (counter solvent) to the solvent mixture. High throughput crystallization techniques can be employed, to prepare crystalline structures, including polymorphs. Drug crystals including polymorphs, methods of preparation, and characterization of drug crystals are disclosed in Solid-State Chemistry of Drugs, S. R. Byrn, R. R. Pfeiffer, and J. G Stowell, 2nd Edition, SSCI, West Lafayette, Ind., 1999.

Seed crystals can be added to any crystallization mixture to promote crystallization. As is clear to the skilled person, seed crystal is used as a means of controlling the growth of a particular crystalline structure or as a means of controlling the particle size distribution of the crystalline product. Accordingly, the calculation of the amount of seed crystal required depends on the size of the available seed crystal and the desired size of the average product particle, as described in "Programmed cooling of batch crystallizers," J. W. Mullin and J. Nyvlt, Chemical Engineering Science, 1971, 26, 369-377. In general, small sized species are needed to effectively control the growth of crystals in the batch. Small sized seed crystals can be produced by sieving, milling, or micronizing of larger crystals, or by solution micro-crystallization. It should be noted that milling or micronizing of crystals does not result in any change in crystallinity of the desired crystal structure (i.e., change to amorphous or to another polymorph).

As used herein, the term "room temperature" or "RT" refers to an ambient temperature of 20 to 25° C. (68-77° F.).

Crystal structures equivalent to the crystal structures described below and claimed herein can exhibit similar, but non-identical, analytical characteristics within a reasonable range of error, depending on test conditions, purity, equipment and other common variables known to those skilled in the art. Accordingly, it will be apparent to those skilled in the art that various modifications and variations can be made in the present invention without departing from the scope and spirit of the present invention. Other embodiments of the present invention will be apparent to those skilled in the art from consideration of the specification of the present invention disclosed herein and based on practice. Applicants intend that the specification and examples be considered as exemplary, but not as limiting the scope thereof.

2. Experimental Materials

The reagents used in the examples of the present invention are commercially available industrial grade or analytical grade reagents. The compound is prepared according to the Example 9 of patent application WO2015032272A1 filed by Jiangsu Hansoh Pharmaceuticals Co., Ltd., and the purity is 95.1% determined by liquid chromatography.

3. Analysis Methods 3.1. X-Ray Powder Diffraction

Those skilled in the art will recognize that an X-ray powder diffraction spectrum can be obtained with a measurement error that depends on the measurement conditions employed. In particular, it is generally known that the intensity in an X-ray powder diffraction pattern can fluctuate depending on measurement conditions employed. It should be further understood that the relative intensity can also vary depending on experimental conditions and, accordingly, the exact intensity should not be taken into account. Additionally, a measurement error of a conventional X-ray powder diffraction angel is usually about 5% or less, and such degree of measurement error should be regarded as belonging to the aforementioned diffraction angles. Consequently, it is to be understood that the crystal structures of the present invention are not limited to the crystal structures that provide X-ray powder diffraction pattern exactly the same as the X-ray powder diffraction pattern depicted in the Figures disclosed herein. Any crystal structures that provide X-ray powder diffraction pattern substantially the same as those disclosed in the Figures fall within the scope of the present invention. The ability to determine substantial identities of X-ray powder diffraction pattern is within the purview of those skilled in the art. Other suitable standard calibrations are known to those skilled in the art. The relative intensities, however, can vary depending on the size and shape of the crystal.

The crystal forms of the compound of the present invention were characterized by their X-ray powder diffraction pattern. Therefore, the X-ray powder diffraction pattern of the salt was collected by a Bruker D8 Discover X-ray powder diffractometer with GADDS (General Area Detector Diffraction System) CS using Cu Kα radiation (1.54 Å) in reflective mode. Tube voltage and current amount for scanning were set to 40 kV and 40 mA, respectively. In the 2θ range of 3.0° to 40°, the sample was scanned for 60 seconds. For peak position represented by 2θ, a corundum standard was used to calibrate the diffractometer. All analysis was usually implemented at 20° C.-30° C. The data was collected and integrated by GADDS using WNT software version 4.1.14T. The diffraction pattern were analyzed by Diffrac-Plus software with version 9.0.0.2 Eva, which was published in 2003. The sample of XRPD was prepared as follows: the sample was placed on a monocrystalline silicon wafer, then the sample powder was pressed by a glass sheet or an equivalent to ensure that the surface of the sample was flat and had a suitable height. Then, the sample holder was placed in the Bruker XRPD instrument, and the X-ray powder diffraction pattern was collected using the instrument parameters described above. The measured difference related to the analysis result of the X-ray powder diffraction was produced by various factors including: (a) the error of sample preparation (e.g., sample height), (b) the instrument error, (c) the calibration error, (d) operator error (including those errors that occur in the determination of peak positions), and (e) properties of the substance (e.g. preferred orientation error). Calibration error and sample height error often lead to shifts of all the peaks in the same direction. In general, the calibration factor will make the measured peak positions consistent with the expected peak positions and in the range of expected 2θ values±0.2°.

3.2. Differential Scanning Calorimetry (DSC)

Differential scanning calorimetry (DSC) tests were carried out on the TA Instruments™ model Q2000. The sample (approximately 1-6 mg) was weighed in an aluminum pan and accurately recorded as a hundred of a milligram, and transferred to the DSC instrument. The instrument was purged with nitrogen at 50 ml/min. Data was collected from room temperature to 350° C. at a heating rate of 10° C./min. The pattern were plotted when the endothermic peaks were downward. However, those skilled in the art will notice that in the DSC measurement, the measured start temperature and maximum temperature vary in a certain degree, depending on heating rate, crystal shape, purity, and other measured parameters.

3.3. Thermogravimetric Analysis (TGA)

Thermogravimetric analysis (TGA) tests were carried out on a TA Instruments™ model Q500. The sample (approximately 10-30 mg) was placed on a pre-weighed platinum pan. The sample was weighed accurately by the instrument and recorded as a thousand of a milligram. The furnace was purged with nitrogen at 100 ml/min. Data was collected from room temperature to 300° C. at a heating rate of 10° C./min.

The present invention is further described by the figures and following examples, which are intended to illustrate the specific embodiments of the present invention and are not to be construed as limiting the scope of the present invention in any way.

Example 1

20 mg of the compound of formula (I) was placed in a 4.0 mL glass vial, then 1 mL of diethylamine was added as a positive solvent, and the mixture was stirred to make it clear. 4.0 mL of water was added slowly as an anti-solvent, and the mixture was stirred by a magnetic stirrer at room temperature (20-25° C.) for 24 hours. The crystalline diethylamine solvate of the compound of formula (I) (referred to as crystal form I herein) was obtained by solid-liquid separation. The X-ray powder diffraction pattern of the crystal form is shown in FIG. 1.

Example 2

50 mg of the compound of formula (I) was placed in a 10.0 mL glass vial, then 5 mL of diethylamine was added as a positive solvent, and the mixture was stirred to make it clear. 5 mg of crystal obtained in Example 1 was added, and the mixture was stirred by a magnetic stirrer at room temperature (20-25° C.) for 24 hours. The crystalline diethylamine solvate of the compound of formula (I) was obtained by solid-liquid separation. The X-ray powder diffraction pattern of the crystal form is substantially the same as FIG. 1.

Example 3

500 mg of the compound of formula (I) was placed in a 100.0 mL round-bottomed flask, then 25 mL of diethylamine was added as a positive solvent, and the mixture was stirred to make it clear. 50 mL of water was added slowly as an anti-solvent, followed by addition of 20 mg of crystal obtained in Example 1. Then, another 50 mL of water was added slowly as an anti-solvent, and the mixture was stirred by a magnetic stirrer at room temperature (20-25° C.) for 24 hours. The crystalline diethylamine solvate of the compound of formula (I) was obtained by solid-liquid separation. The X-ray powder diffraction pattern of the crystal form is substantially the same as FIG. 1.

The purity of the resulting sample is 99.5% determined by high performance liquid chromatography, which has a substantial improvement in comparison with the purity (95.1%, determined by liquid chromatography) of the material for crystallization (prepared according to the Example 9 of the patent application WO2015032272A1 filed by Jiangsu Hansoh Pharmaceuticals Co., Ltd.). It can meet the requirement for clinical development, and overcomes the technical defect in prior art where the dissolution of the amorphous solid and solvent removal are carried out repeatedly, but an amorphous solid with low purity is stilled obtained. It can be seen that the preparation of diethylamine solvate from an amorphous material in the present invention can not only provide a compound in a solid form, especially in a crystalline form, but also significantly improve the purity of the sample, which reaches the level for clinical use.

Figure 2:
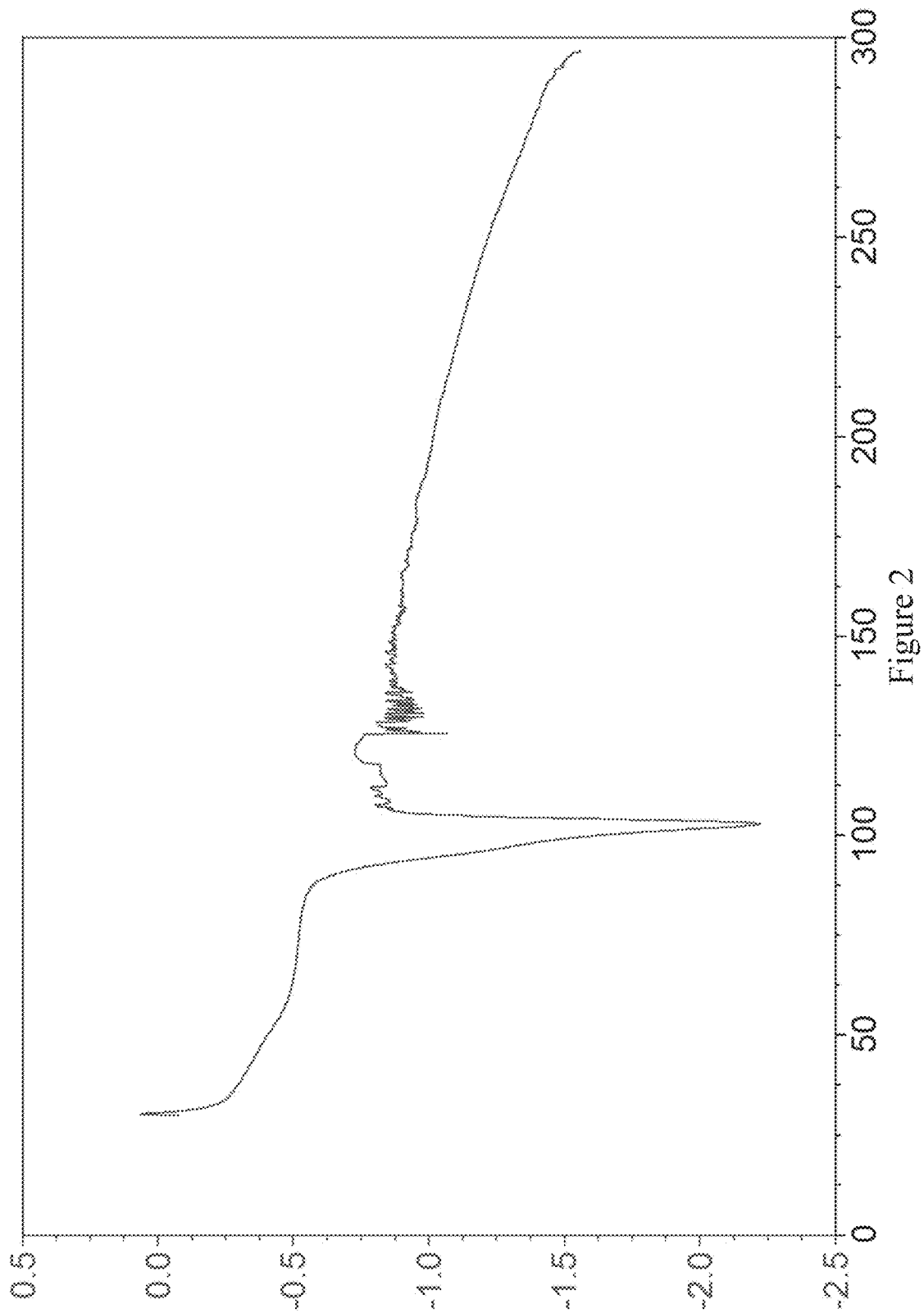
FIG. 2 shows the differential scanning calorimetry pattern of crystal form I; X-axis represents the temperature (° C.), Y-axis represents the heat flux (W/G).

The DSC analysis results of crystal form I obtained in Examples 1-3 showed that there was a characteristic endothermic peak at 102.8±2° C., as shown in FIG. 2.

Figure 3:
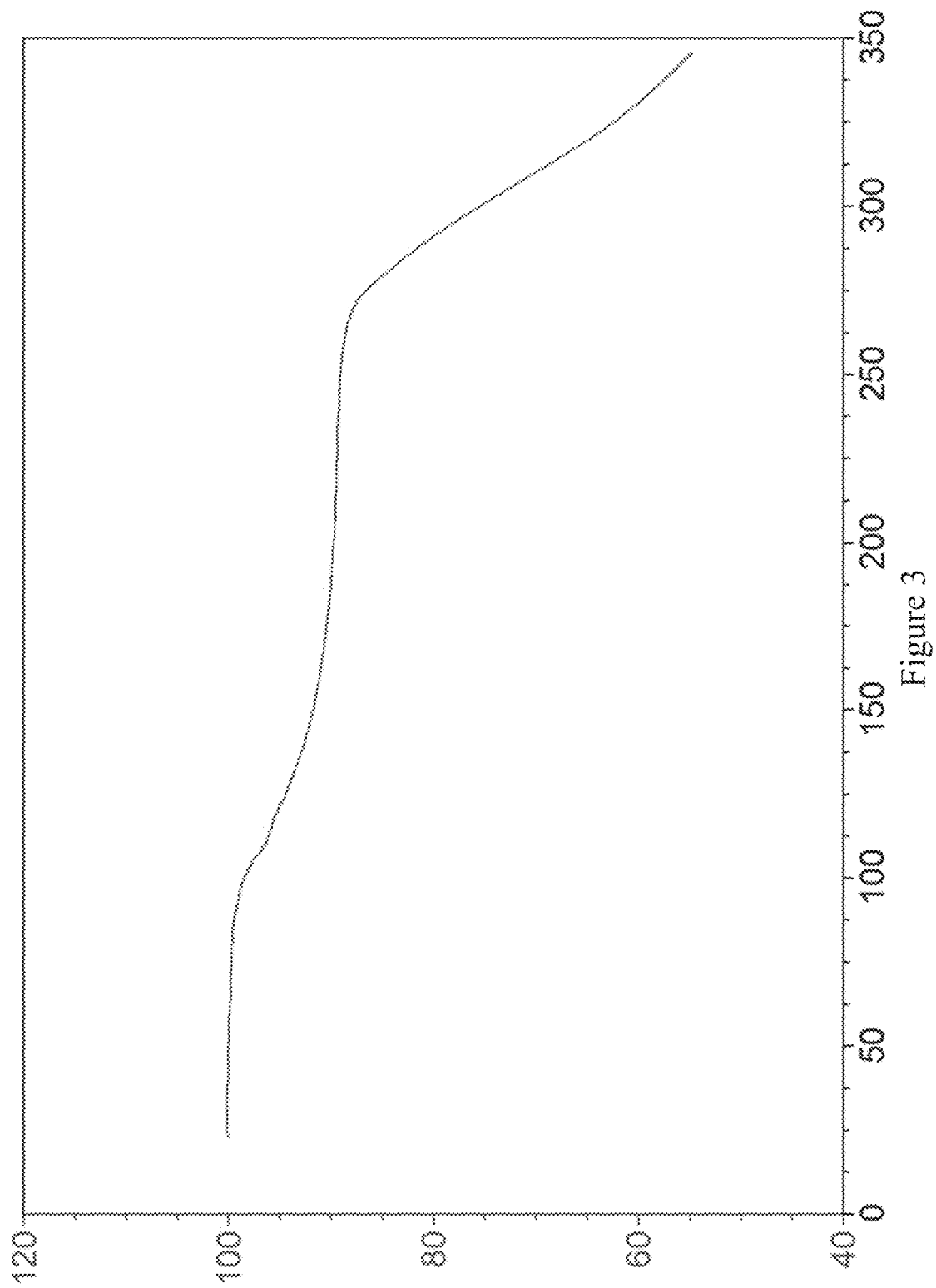
FIG. 3 shows the thermogravimetric analysis pattern of crystal form X-axis represents the temperature (° C.), Y-axis represents the percentage of weight loss (%).

The TGA analysis results of crystal form I obtained in Examples 1-3 showed that when the sample is heated to 93.5° C., the weight loss of the sample was 1.02%, as shown in FIG. 3. The preliminary study showed that it was surface adsorption of water, which can be negligible.

Figure 4:
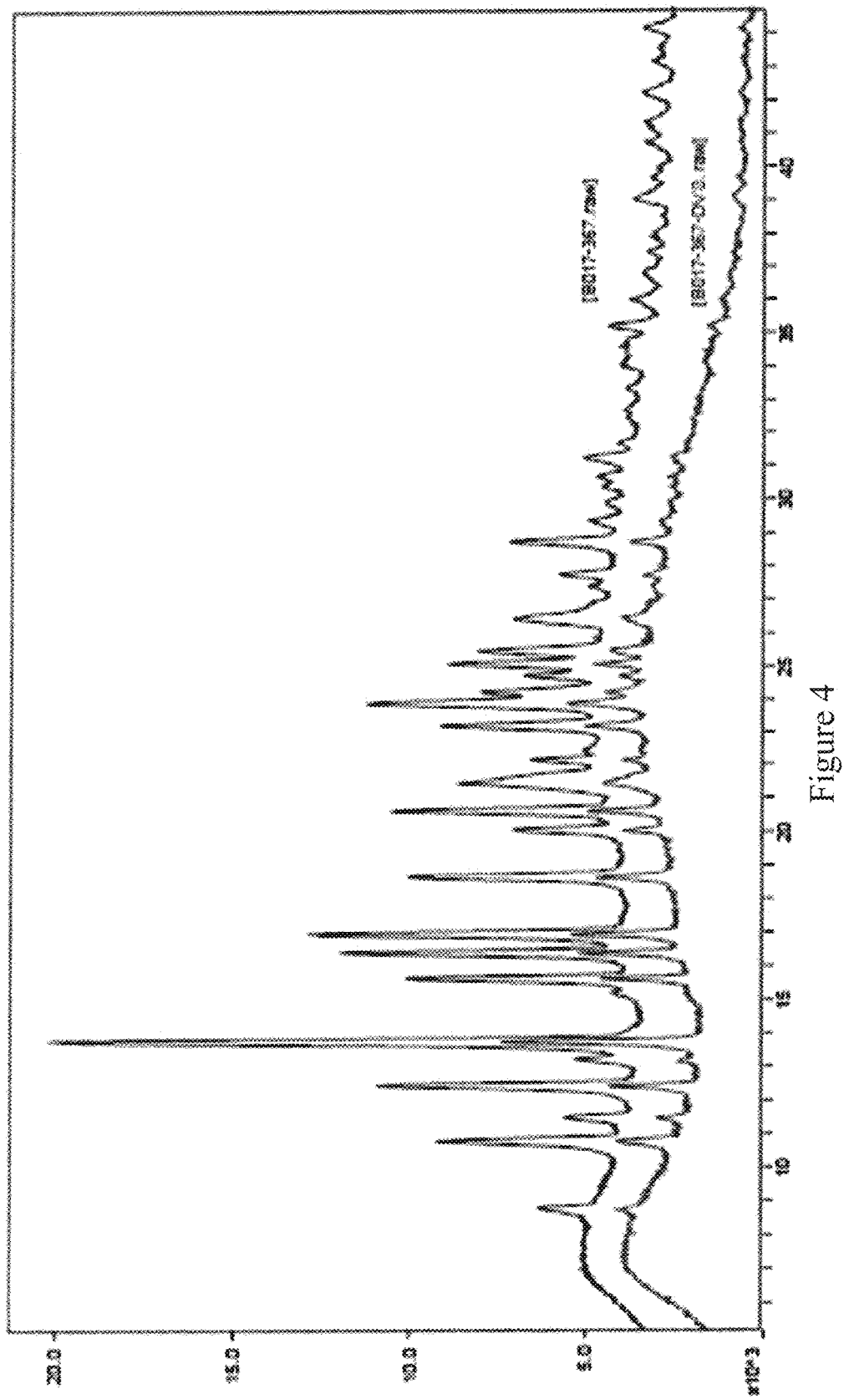
FIG. 4 shows the X-ray powder diffraction pattern of crystal form I before (upper) and after (lower) the dynamic moisture adsorption test. X-axis represents the diffraction peak angle 2θ (°), Y-axis represents the intensity of the peak.

According to the dynamic moisture adsorption test on sample of crystal form I, the amount of water absorption increases along with the increase of humidity between 0% RH and 80% RH under a condition of 25° C., and the weight change is 0.286%. According to the Guidelines for drug hygroscopicity test described in "Pharmacopoeia of the People's Republic of China (2010 edition)", this sample is slightly hygroscopic. Under the normal storage condition (i.e. 25° C., 60% humidity), the amount of water absorption was about 0%; under the accelerated test condition (i.e. 75% humidity), the amount of water absorption was about 0.191%; and under the extreme condition (i.e. 90% humidity), the amount of water absorption was about 1.049%. FIG. 4 shows the comparison diagram of XRPD patterns before and after the dynamic moisture adsorption test. It can be seen that the crystal form of the sample is unchanged before and after the dynamic moisture adsorption test.

Example 4

5 mg of the compound of formula (I) was placed in a 2.0 mL glass vial, then 0.2 mL of diethylamine was added as a positive solvent, and the mixture was stirred to make it clear. 1.0 mL of water was added slowly as an anti-solvent, and the mixture was left to stand at room temperature (20-25° C.) for 1 week. The single crystal of diethylamine solvate of the compound of formula (I) was obtained by solid-liquid separation.

The single crystal data were collected on the Bruker Apex II single crystal test system by using Mok$\alpha$ radiation ($\lambda$=0.71073 Å). The indexing and processing of the intensity data measured were carried out on the Collect program button of HKL2000 software package. The temperature was 296K during the process of the crystal data collecting.

Figure 5:
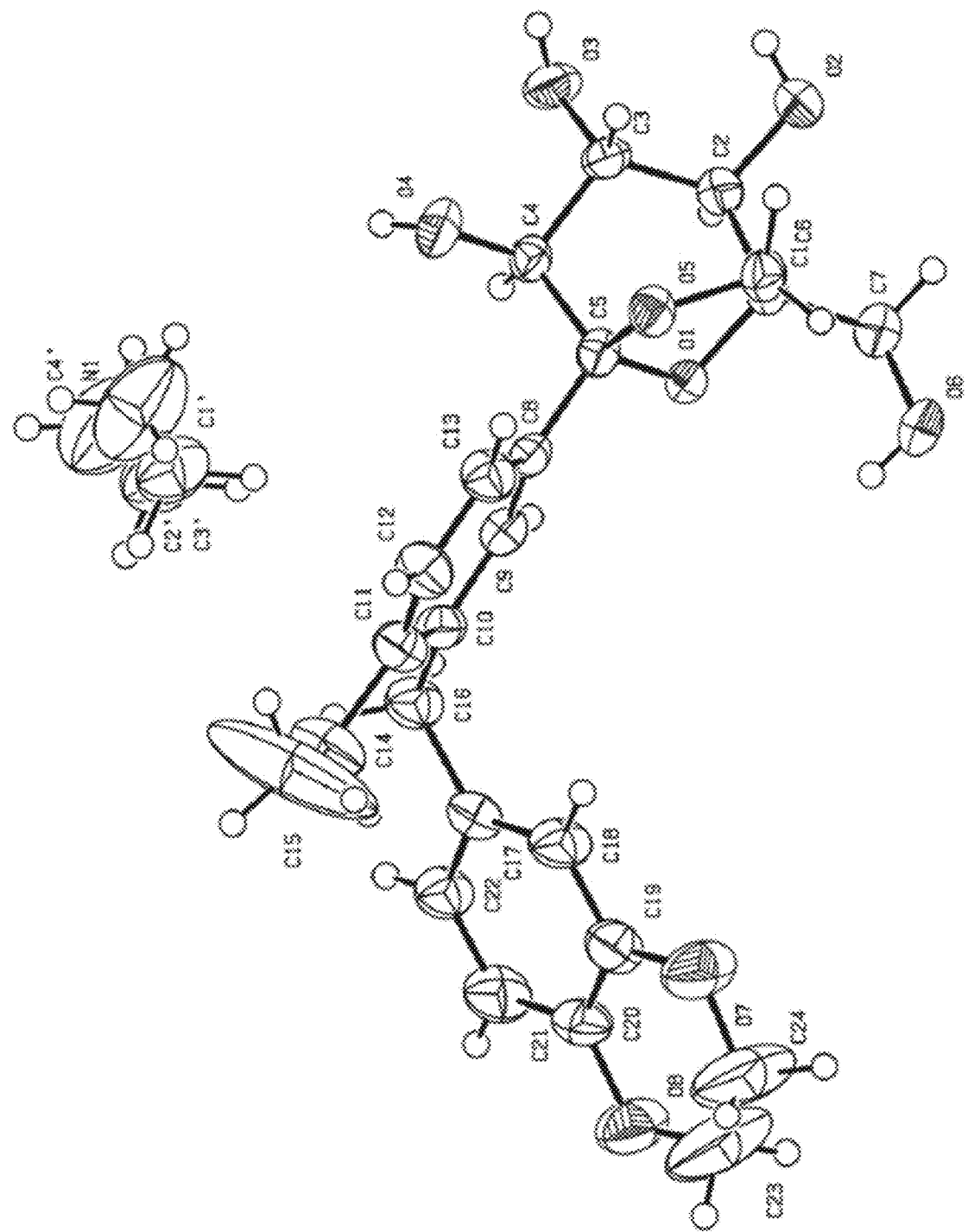
FIG. 5 shows the single crystal structure diagram of crystal form I.
Figure 6:
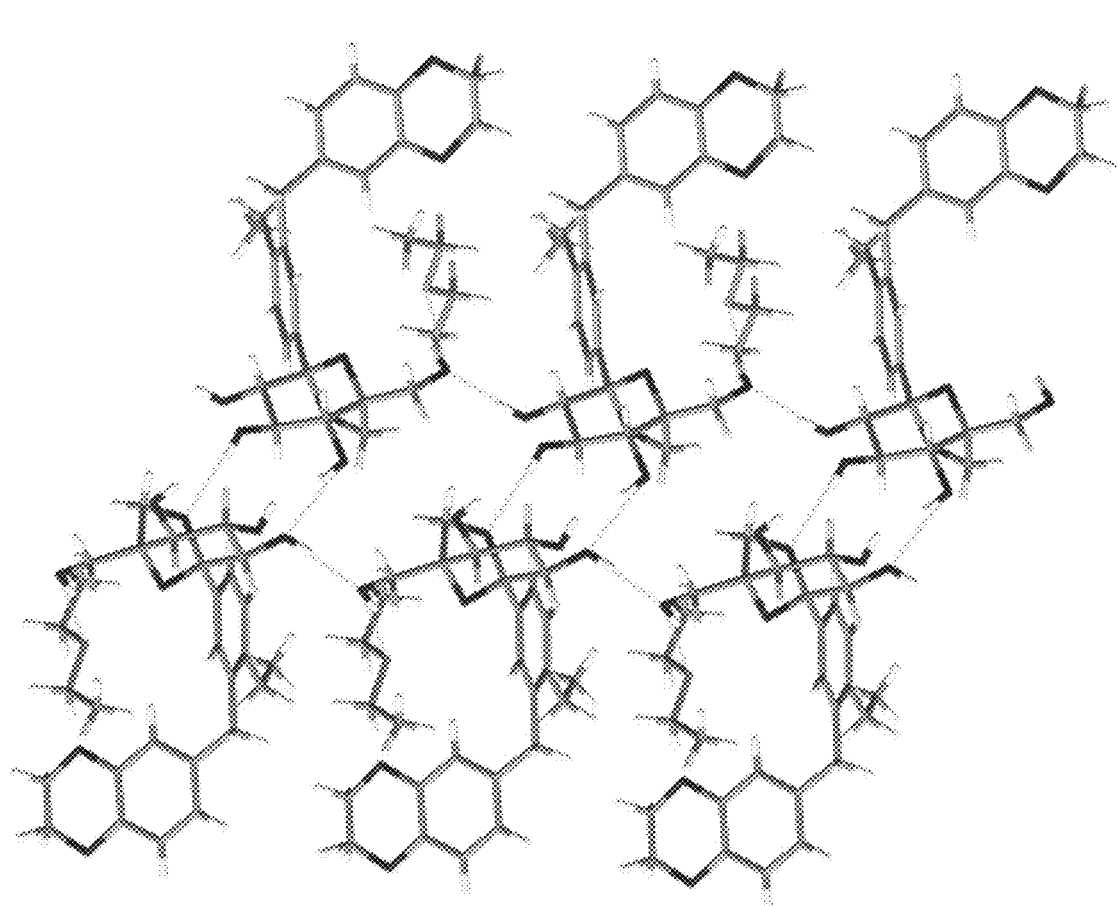
FIG. 6 shows the unit cell stacking diagram of crystal form I.
Figure 7:
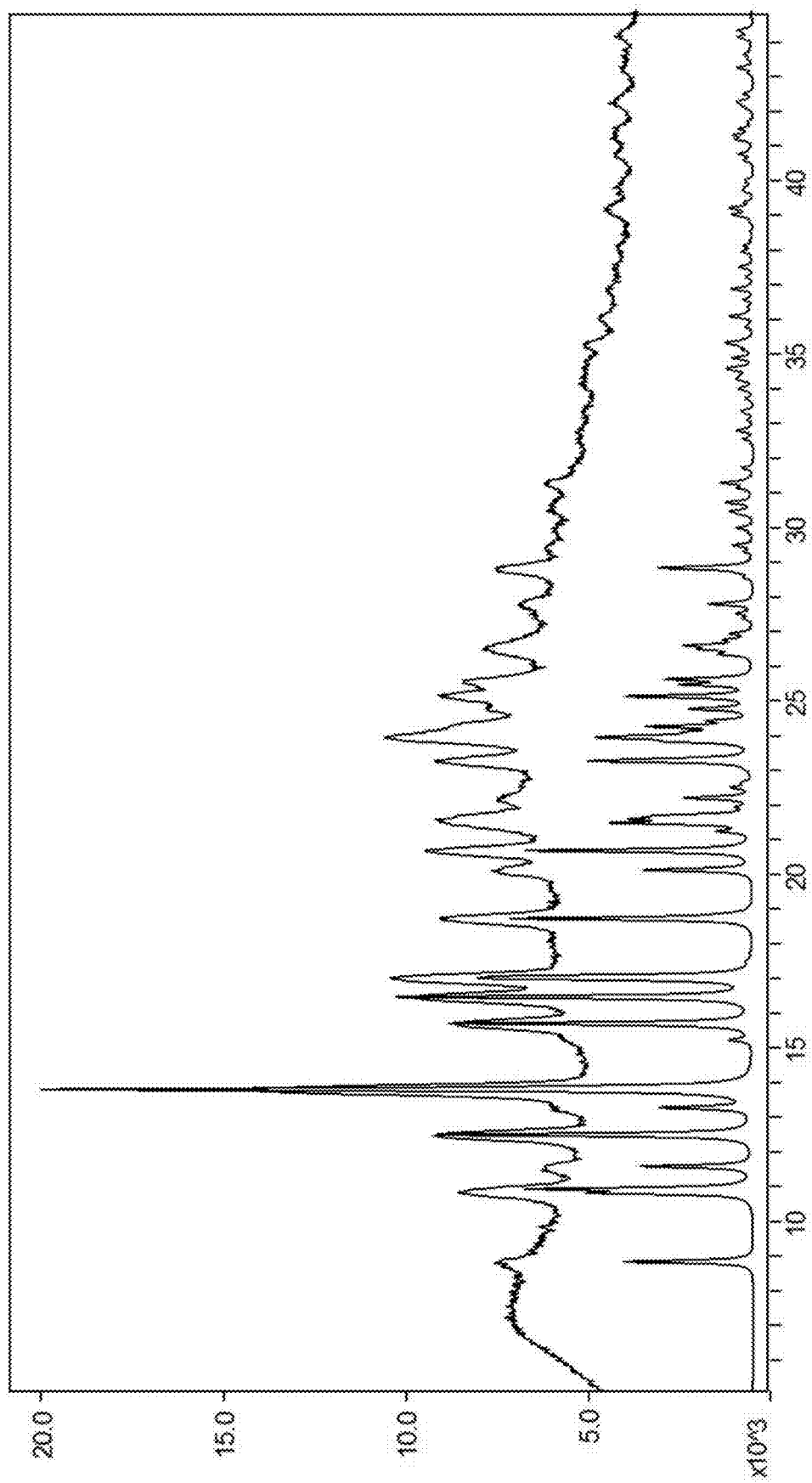
FIG. 7 shows the comparison diagram between the single crystal simulated powder diffraction pattern (lower) and the measured powder diffraction pattern (upper) of crystal form I. X-axis represents the diffraction peak angle 2θ (°), Y-axis represents the intensity of the peak.
Figure 8:
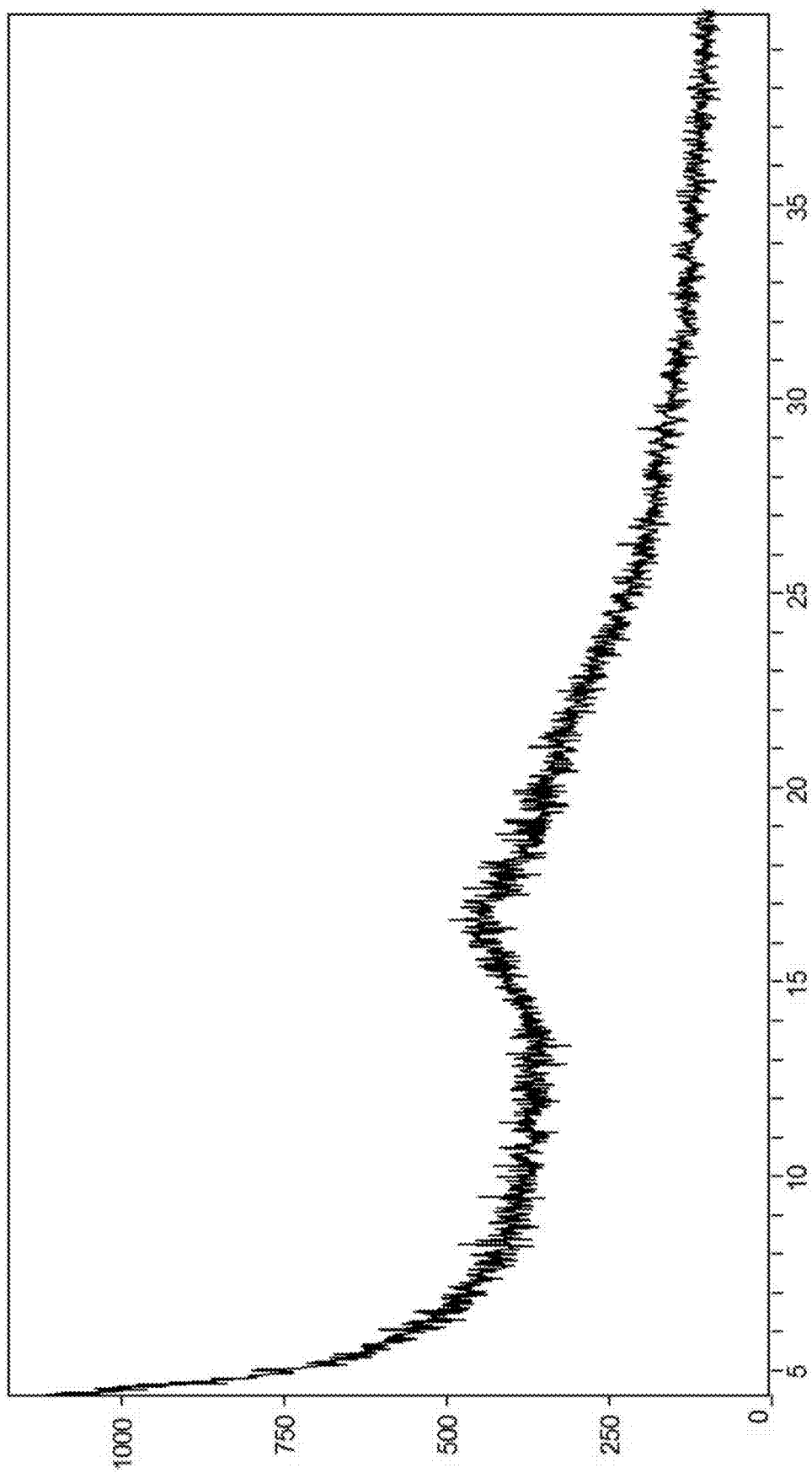
FIG. 8 shows the X-ray powder diffraction pattern of amorphous compound of formula (I); X-axis represents the diffraction peak angle 2θ (°), Y-axis represents the intensity of the peak.

FIG. 5 shows the structure diagram of crystal form I, and FIG. 6 shows the structure stacking diagram of crystal form I. FIG. 7 shows the comparison diagram between the single crystal simulated powder diffraction pattern and the measured powder diffraction pattern of crystal form I. Experiments showed that the powder crystal obtained in Example 1 is substantially pure. The unit cell parameters of crystal form I are shown in Table 2:

TABLE 2

Molecular formula: $C_{28}H_{38}NO_8$
$M_r$ = 516.59
orthogonal system, space group, $P2_12_12_1$
a = 8.2642 (4) Å
b = 8.3582 (4) Å
c = 39.994 (2) Å
Unit cell volume V = 2762.5 (2) Å$^3$
Z = 4
F(000) = 1108
Density $D_x$ = 1.242 Mg m$^{-3}$
Mo K radiation, = 0.71073 Å
Linear absorption coefficient = 0.09 mm$^{-1}$
Test temperature T = 296K
Single crystal size: 1 × 0.7 × 3 mm Example 5

The stress study on the physical stability and chemical stability of the diethylamine solvate of the compound of formula (I) and the amorphous compound of formula (I) were carried out. The diethylamine solvate of the compound of formula (I) obtained in Example 3 and the amorphous compound of formula (I) were placed in glass vials respectively in duplicate, about 10 mg each sample. These samples for stability test were placed in an incubator at 80° C. for one week. After being placed for one week, one sample was used for the chemical purity analysis by HPLC method. The other sample was used for the crystal characterization by XRPD. The physical stability and chemical stability of the two solids are shown in Table 3.

TABLE 3

| Samples for stability test | Initial state of the samples | | After being placed for one week at 80° C. | |
|---|---|---|---|---|
| | Chemical purity | Physical state | Chemical purity | Physical state |
| Diethylamine solvate of the compound of formula (I) | 99.5% | White powder | 99.5% | White powder, XRPD showed that the crystal form was unchanged |
| Amorphous compound of formula (I) | 95.1% | Light yellow powder | 90.2% | Immediately melted into a glassy state after being put into an incubator |

According to the above stress stability tests, the diethylamine solvate of the compound of formula (I) had obvious advantages in physical stability and chemical stability in comparison with the amorphous compound of formula (I). The sample of the diethylamine solvate of the compound of formula (I) did not degrade at high temperature, the chemical purity was substantially unchanged, and the crystal form also remained the same substantially. However, the amorphous compound of formula (I) changed and degraded immediately after being placed at high temperature, making it difficult to ensure the product quality. It is known that in the field of drug development, the physical stability and chemical stability of a compound are critical to production, storage, transportation, formulation process, validity period of the drug, and the like. Therefore, in comparison with the amorphous compound of formula (I), the diethylamine solvate of the compound of formula (I) developed by the present invention is more in line with clinical research needs, and more advantageous for pharmaceutical development.

In summary, the amine solvate of the compound of formula (I) developed by the present invention has higher physical stability and chemical stability in comparison with the amorphous aggregation state. In particular, the product of crystal form I obtained in the Examples has high purity, high stability and low hygroscopicity, which facilitate the production, transportation and storage of the drug. The unit operations during the process such as purification, decolorization, filtration, and the like are also simple and easy to carry out, so it has obvious advantages. Therefore, the amine solvate of the compound of formula (I) of the present invention has significant improvements in comparison with the previously amorphous compound of formula (I), and meets the requirement of clinical drug development.

Finally, it should be noted that the above examples are used only to illustrate the technical solution of the present invention, but are not intended to limit the scope of the present invention. Although the present invention has been described in detail with reference to the preferred examples, the person skilled in the art would understand that the technical solution of the present invention can be modified or equivalently varied without departing from the spirit and scope of the present invention, and such modifications and variations should be included in the claims of the present invention.

What is claimed is:

1. An amine solvate of a compound of formula (I):

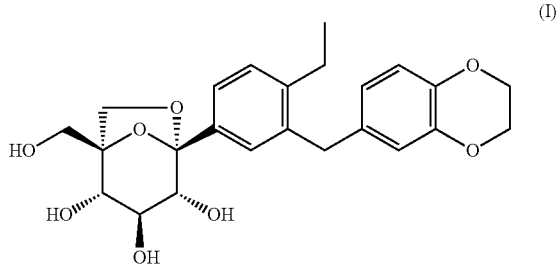 [SMILES: CCc1ccc([C@]23OC[C@](CO)(O2)[C@@H](O)[C@H](O)[C@H]3O)cc1Cc1ccc2c(c1)OCCO2]

wherein the amine is selected from the group consisting of methylamine, dimethylamine, ethylamine, diethylamine, propylamine, dipropylamine, tripropylamine, 1,2-dimethylpropylamine, cyclopropylamine, diisopropylamine, triethylamine, n-butylamine, isobutylamine, tert-butylamine, sec-butylamine, diisobutylamine, hexylamine, dicyclohexylamine, decylamine, dodecylamine, triethanolamine, allylamine, ethanolamine, 3-propanolamine, isopropanolamine, diisopropanolamine, triisopropanolamine, dimethylethanolamine, diethylethanolamine, ethylenediamine, 1,3-propanediamine, 1,4-butanediamine, 1,5-pentanediamine, 1,6-hexanediamine, morpholine and piperazine.

2. The amine solvate of the compound of formula (I) according to claim 1, wherein it is a solid compound.

3. The amine solvate of the compound of formula (I) according to claim 1, wherein it is a diethylamine solvate of the compound of formula (I).

4. The amine solvate of the compound of formula (I) according to claim 3, wherein the X-ray powder diffraction pattern of the diethylamine solvate of the compound of formula (I) comprises peaks at diffraction angle (2θ) of 13.78±0.2°, 17.02±0.2°, 16.48±0.2°, and 12.46±0.2°.

5. The amine solvate of the compound of formula (I) according to claim 3, wherein the unit cell of the diethylamine solvate of the compound of formula (I) is orthogonal system, space group, P212121, a=8.2642 (4) Å, b=8.3582 (4) Å, c=39.994 (2) Å, and the unit cell volume is 2762.5 (2) Å$^3$.

6. A process for preparing the amine solvate of the compound of formula (I) according to claim 1, comprising the following steps of:
step 1): contacting the compound of formula (I) with an amine reagent;
step 2): adding an anti-solvent until the solution appears turbid, or adding a seed crystal, or a combination thereof, then continuing to precipitate a crystal; and
step 3): separating solid-liquid to obtain the amine solvate of the compound of formula (I).

7. The process for preparing the amine solvate of the compound of formula (I) according to claim 6, wherein the amine reagent in step 1) is a pure liquid amine reagent, an aqueous amine reagent or a mixture of an amine reagent and an organic solvent, and the amine reagent is selected from the group consisting of methylamine, dimethylamine, ethylamine, diethylamine, propylamine, dipropylamine, tripropylamine, 1,2-dimethylpropylamine, cyclopropylamine, diisopropylamine, triethylamine, n-butylamine, isobutylamine, tert-butylamine, sec-butylamine, diisobutylamine, hexylamine, dicyclohexylamine, decylamine, dodecylamine, triethanolamine, allylamine, ethanolamine, 3-propanolamine, isopropanolamine, diisopropanolamine, triisopropanolamine, dimethylethanolamine, diethylethanolamine, ethylenediamine, 1,3-propanediamine, 1,4-butanediamine, 1,5-pentanediamine, 1,6-hexanediamine, morpholine and piperazine.

8. The process for preparing the amine solvate of the compound of formula (I) according to claim 6, wherein dissolving the compound of formula (I) in an amine reagent, or dissolving the compound of formula (I) in an organic solvent, followed by the addition of an amine reagent in step 1).

9. The process for preparing the amine solvate of the compound of formula (I) according to claim 6, wherein the anti-solvent in step 2) is selected from the group consisting of water, n-heptane, n-hexane, isooctane, pentane, cyclohexane, cyclopentane, diethyl ether and a mixture thereof.

10. The process for preparing the amine solvate of the compound of formula (I) according to claim 7, wherein the organic solvent is selected from the group consisting of methanol, ethanol, n-propanol, isopropanol, n-butanol, acetonitrile, acetone, methyl ethyl ketone, tetrahydrofuran, dioxane, N,N-dimethylformamide, dimethyl sulfoxide, ethyl acetate, isopropyl acetate, dichloromethane, trichloroethane, carbon tetrachloride, methyl tert-butyl ether, diisopropyl ether, benzene, toluene, xylene and a mixture thereof.

11. A pharmaceutical composition comprising a therapeutically effective amount of the amine solvate of the compound of formula (I) according to claim 1, and a pharmaceutically acceptable carrier.

12. The amine solvate of the compound of formula (I) according to claim 1 or the pharmaceutical composition according to claim 11 for use as a SGLTs inhibitor.

13. The amine solvate of the compound of formula (I) according to claim 1 or the pharmaceutical composition according to claim 11 for use in treating or delaying the development or the attack of diabetes, diabetic retinopathy, diabetic neuropathy, diabetic nephropathy, insulin resistance, hyperglycemia, hyperinsulinemia, elevated levels of fatty acids or glycerol, hyperlipidemia, obesity, hypertriglyceridemia, X syndrome, diabetes complications, atherosclerosis or hypertension.

14. A method for inhibiting SGLTs, comprising administrating a therapeutically effective amount of the amine solvate of the compound of formula (I) according to claim 1 or the pharmaceutical composition according to claim 11 to a patient in need thereof.

15. A method for treating diabetes, diabetic retinopathy, diabetic neuropathy, diabetic nephropathy, insulin resistance, hyperglycemia, hyperinsulinemia, elevated levels of fatty acids or glycerol, hyperlipidemia, obesity, hypertriglyceridemia, X syndrome, diabetes complications, atherosclerosis or hypertension, comprising administrating a therapeutically effective amount of the amine solvate of the compound of formula (I) according to claim 1 or the pharmaceutical composition according to claim 11 to a patient in need thereof.

16. The amine solvate of the compound of formula (I) according to claim 1, wherein it is a crystalline compound.

17. The amine solvate of the compound of formula (I) according to claim 4, wherein the X-ray powder diffraction pattern of the diethylamine solvate of the compound of formula (I) further comprises peaks at diffraction angle (2θ) of 23.94±0.2°, 18.74±0.2°, 18.76±0.2°, 15.72±0.2°.

18. The amine solvate of the compound of formula (I) according to claim 17, wherein the X-ray powder diffraction pattern of the diethylamine solvate of the compound of formula (I) further comprises peaks at diffraction angle (2θ) of 10.82±0.2°, 21.58±0.2°, 23.26±0.2°, 25.16±0.2°, 25.58±0.2°, and 24.26±0.2°.

19. The amine solvate of the compound of formula (I) according to claim 3, wherein the X-ray powder diffraction pattern of the diethylamine solvate of the compound of formula (I) comprises substantially the same peaks at diffraction angles (2θ) as shown in Table 1.

* * * * *